United States Patent [19]

Nakamura et al.

[11] Patent Number: 4,776,976

[45] Date of Patent: Oct. 11, 1988

[54] O/W TYPE EMULSION COMPOSITION

[75] Inventors: Tohru Nakamura, Funabashi; Toshiyuki Suzuki, Ichikawa, both of Japan

[73] Assignee: Kao Corporation, Tokyo, Japan

[21] Appl. No.: 46,288

[22] Filed: May 6, 1987

[30] Foreign Application Priority Data

May 6, 1986 [JP] Japan .................. 61-103448

[51] Int. Cl.$^4$ .................. B01F 17/28; B01F 17/14
[52] U.S. Cl. .................. 252/312; 252/356; 514/561; 514/938; 514/943
[58] Field of Search ........ 252/312, DIG. 7, DIG. 17, 252/356; 514/561, 938, 939, 943

[56] References Cited

U.S. PATENT DOCUMENTS

| | | | |
|---|---|---|---|
| 2,109,842 | 3/1938 | Harris | 252/312 X |
| 4,206,070 | 6/1980 | Jones | 252/351 X |
| 4,400,295 | 8/1983 | Ootsu et al. | 252/312 X |
| 4,661,343 | 4/1987 | Zabotto et al. | 514/938 X |

*Primary Examiner*—Herbert B. Guynn
*Attorney, Agent, or Firm*—Oblon, Fisher, Spivak, McClelland & Maier

[57] ABSTRACT

A composition comprising; (A) a basic amino acid salt of a higher aliphatic phosphate represented by the following formula (I):

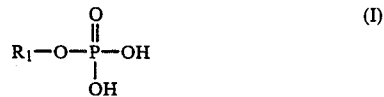

in which $R_1$ is an alkyl or alkenyl group having from 12 to 22 carbon atoms, and (B) an α-monoalkyl glyceryl ether represented by the following formula (II):

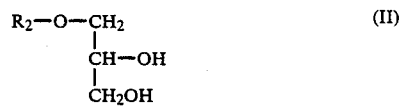

in which $R_2$ is an alkyl group having from 12 to 24 carbon atoms. The composition provides an O/W type emulsion suitable for use as cosmetics which has a small viscosity decrease at a high temperature and a small viscosity increase at a low temperature, is stable during storage over a long period of time, provides good feelings and a moisture retaining effect on use to the skin, and yet has an excellent safety.

4 Claims, 2 Drawing Sheets

O/W TYPE EMULSION COMPOSITION

BACKGROUND OF THE INVENTION

1. Field of the Invention

This invention relates to an oil in water (hereinafter abbreviated to "O/W") type emulsion composition comprising L-arginine salt of a higher aliphatic phosphate, and an α-monoalkyl glyceryl ether. More particularly, the invention is directed to an O/W type emulsion composition which has a small viscosity decrease at a high temperature and a small viscosity increase at a low temperature, is stable during storage over a long period of time, provides good feelings and a moisture retaining effect on use to the skin, and yet has an excellent safety.

2. Prior Art

In recent years, it is considered desirable that the skin cosmetics has a pH range of 5.0–6.5 which is commensurate with the pH range of the human skin. Thus, there is a tendency of increasing use of such weakly acidic emulsion type cosmetics. In order to produce the weakly acidic emulsion composition there has been conventionally used emulsifiers such as non-ionic surface active agents of an ethylene oxide addition type, alkyl sulfates, salts of N-acylated glutamic acid and the like, and emulsification assistant agents, including, for example, higher alcohols such as cetanol or higher fatty acids such as stearic acid.

The aforementioned emulsifiers, however, possess a drawback in that the viscosity of the emulsions prepared therefrom decreases at a high temperature and increases at a low temperature. In particular, the easiness of taking out the emulsion from the bottle, the solidity of the cream, and the properties of the cream for handling with fingers have a dependency on the temperature at which the product is used. Moreover, the change of the temperature causes the gloss of the cream to diminish and gives adverse effects on the spreadability of the cream and its fitness or affinity to the skin.

Therefore, there has been a demand for suitable combination of emulsifiers and emulsification assistant agents which may provide weakly acidic emulsions and creams of which viscosity, appearance, solidity and feelings on use do not change by the change of temperature.

SUMMARY OF THE INVENTION

The inventors have made earnest studies for solving the aforementioned problems in the conventional emulsions and creams, and as a result found that the combination of a weakly acidic emulsifier obtained by neutralizing a specific higher aliphatic phosphate with a basic amino acid and an α-monoalkyl glyceryl ether could give O/W type emulsion compositions possessing the following favorable characteristics, that is; a constant viscosity over a wide range of temperatures, i.e., exhibiting a small viscosity decrease at a high temperature and a small viscosity increase at a low temperature; an excellent storage stability over a long period of time; the properties of providing a good feeling on use and moisture retaining effects to the skin; and the outstanding safety. Such findings has lead to the completion of this invention.

Accordingly an object of this invention is to provide an oil in water type emulsion composition comprising;

(A) a basic amino acid salt of a higher aliphatic phosphate represented by the following formula (I):

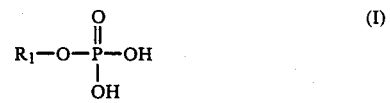

in which $R_1$ is an alkyl or alkenyl group having from 12 to 22 carbon atoms, and (B) an α-monoalkyl glyceryl ether represented by the following formula (II):

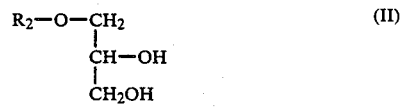

in which $R_2$ is an alkyl group having from 12 to 24 carbon atoms.

The above and other objects, features and advantages of the present invention will become apparent from the following description and the appended claims.

DETAILED DESCRIPTION OF THE INVENTION AND PREFERRED EMBODIMENTS

Figure 1:
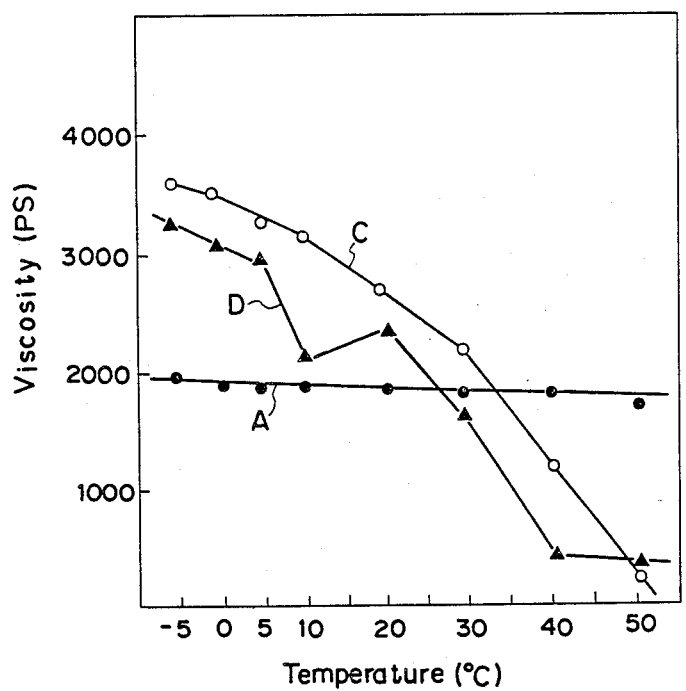
FIGS. 1 and 2 are the drawings showing the temperature-viscosity relations of compositions of the present invention and compositions of comparative products which are obtained by Examples 1 and 2, respectively. The viscosities are expressed in poise in FIG. 1 and in centipoise in FIG. 2.

Higher aliphatic phosphates used for the preparation of the component (A) of this invention may be a linear saturated aliphatic phosphate such as monolauryl phosphate and monocetyl phosphate, an unsaturated aliphatic phosphate such as monooleyl phosphate, and, branched saturated aliphatic phosphate such as mono-i-stearyl phosphate. Among them, linear saturated aliphatic phosphates are particularly preferred.

Basic amino acids to neutralize these higher aliphatic phosphate may be, for example, arginine, lysine, ornithine, histidine, δ-hydroxylysine and the like. The amount of the basic amino acids to be used for preparing the component (A) can be determined according to the pH of the aimed emulsions. Taking the case of L-arginine as an example, a generally preferred amount is 0.2–1.8 mole per 1 mole of the phosphate, among which the particularly preferable range is 0.4–1.4 mole. This component (A) may be either prepared in advance separately by neutralizing the higher aliphatic phosphate with basic amono acids in a batch independent from the emulsion composition, or prepared by adding these two ingredients directly to the emulsion composition system.

Among α-monoalkyl glyceryl ethers of the component (B) of this invention, particularly preferred are α-monopalmityl glyceryl ether and α-monostearyl glyceryl ether in which $R_2$s of the formula (II) are 16 and 18, respectively.

The amount of the component (A) to be incorporated in the composition of this invention, as expressed by weight percent of the higher aliphatic phosphate therein, may be 0.01–5 wt%, particularly preferably 0.03–3 wt%. The amount of the component (B) to be incorporated may be 0.1-20 parts by weight, preferably 0.3-12 parts by weight, per 1 part by weight of the component (A).

The O/W type emulsion composition of this invention (hereinafter referred to as the "inventive composition") can be prepared according to the conventional methods by incorporating, in addition to the above components (A) and (B), oils and water, and agitating until it becomes homogeneous. Oils which may be used for preparing the inventive composition are those generally used as cosmetics base materials. Examples include; waxes such as beeswax, lanolin, carnauba wax and candelilla wax; triglyceride such as castor oil and olive oil; hydrocarbons such as cerecine, liquid paraffin, petrolatum and squalane; fatty acids such as stearic acid and palmitic acid; higher alcohols such as cetanol and stearyl alcohol; and ester oils such as cetyl 2-ethylhexanoate and octyldodecyl myristate. The amount of oils to be incorporated to the inventive composition are arbitrarily determined, although they may be in the range of from 1 to 70 wt% of the composition. On the other hand the amount of water in the inventive composition may be 20-90 wt%.

A still more stable emulsion can be prepared according to the present invention by incorporating a non-ionic surface active agent. Enumerated as examples of suitable non-ionic surface active agents are; non-ionic hydrophilic surface active agents, including polyoxyethylene (hereinafter abbreviated to "POE") higher alcohol ethers, POE higher fatty acid esters, POE hydrogenated castor oil derivatives, POE glycerine mono-fatty acid esters and sucrose fatty acid esters; and non-ionic lipophilic surface active agents, including glycerine mono-fatty acid esters and sorbitan fatty acid esters. These non-ionic surface active agents may be incorporated in the inventive composition in the amount of 0.5-10 times by weight of the component (A).

The other ingredients known as additives of cosmetics may be further added to the O/W type emulsion composition of this invention as required. Such ingredients include humectants, thickners, perfumes, preservatives, colorants, pigments and the likes.

Examples of the humectants are propylene glycol, glycerine, polyglycerine, polyethylene glycol, sorbitol, sucrose, maltitol and the like. One or more than two of these compounds may be incorporated to the inventive composition in the amount generally of 2-20 wt%.

The thickners, or the viscosity increasing agents, used for the inventive composition are, for example, polyvinyl alcohol, carboxyvinyl polymer and montmorillonite.

O/W type emulsion compositions of this invention may be made into various forms such as, for example, vanishing cream, liquid emulsion, cold cream, cleansing cream, hair cream, foundation cream and hand cream.

This invention will be hereinafter described in more detail by way of examples.

Example 1

The emulsions of the formulation as shown in Table 1 were prepared according to the method described below. The state of the emulsions, the average size of the emulsion particles, the appearance, the stability after having been left over for one month at room temperature and 40° C. were observed on each of the emulsions prepared. The feelings on use of the emulsions were organoleptically evaluated by a panel of experts. Furthermore, the viscosities at temperatures from −5° C. up to 50° C. were measured to obtain the temperature-solidity relations of the emulsions. The results are shown in Table 2 and the appended FIG. 1.

<Preparation of the Emulsions>

The oil phase was heated to 70°-80° C. and allowed to melt while being agitated, to which the water phase with its ingredients having been dissolved under agitation and heating at 70°-80° C. was added to effect the emulsification. The thus obtained emulsion was cooled down to 50° C., whereupon the perfume was added, and the mixture was further cooled down to a temperature of 20°-30° C.

TABLE 1

| Component | Inventive Products A | Inventive Products B | Comparative Products C | Comparative Products D |
|---|---|---|---|---|
| Oil Phase | | | | |
| Olive oil | 10.0 | 10.0 | 10.0 | 10.0 |
| Liquid paraffin | 10.0 | 10.0 | 10.0 | 10.0 |
| Monostearyl phosphate | 2.0 | 2.0 | 2.0 | 2.0 |
| Cetanol | — | — | 3.0 | — |
| α-monopalmityl glyceryl ether | 3.0 | — | — | — |
| α-monostearyl glyceryl ether | — | 3.0 | — | — |
| Stearic acid | — | — | — | 3.0 |
| Water Phase | | | | |
| L-arginine | 0.9 | 0.9 | 0.9 | 0.9 |
| Methyl paraben | 0.1 | 0.1 | 0.1 | 0.1 |
| Ion exchanged water | balance | balance | balance | balance |
| Perfume | small amount | small amount | small amount | small amount |

TABLE 2

| | Inventive Products A | Inventive Products B | Comparative Products C | Comparative Products D |
|---|---|---|---|---|
| State of emulsion | Good | Good | Good | Good |
| Particle size of emulsion (μm) | 1.2 | 1.1 | 1.3 | 1.4 |
| Appearance immediately after preparation | Good | Good | Good | Good |
| Stability after stored for one month: | | | | |
| at room temp. | Good | Good | Good | Good |
| at 40° C. | Good | Good | Pretty Good | Pretty Good |
| Organoleptic Evaluation * | | | | |
| Easiness in taking out with finger | E | E | RB | RB |
| Spreadability on the skin | E | E | RB | RB |
| Fitness to the skin | E | E | RB | B |

* Organoleptic Evaluation
E: Excellent
PG: Pretty Good
RB: Rather Bad
B: Bad

As shown in Table 2 and FIG. 1, the creams not containing the α-monoalkyl glyceryl ether exhibited the decrease in its viscosity at a high temperature and the increase at a low temperature. On the other hand, those containing the α-monoalkyl glyceryl ether had almost constant viscosities at all the tested temperatures while giving a good feelings on use.

Example 2

The emulsions of the formulation as shown in Table 3 were prepared according to the method described below. The state of the emulsions, the average size of the emulsion particles, the appearance, the stability after having been left over for one month at room temperature and 40° C. were observed on each of the emulsions prepared. The feelings on use of the emulsions were organoleptically evaluated by a panel of experts. Furthermore, the viscosities at temperatures from −5° C. up to 50° C. were measured to obtain the temperature-solidity relations of the emulsions. The results are shown in Table 4 and the appended FIG. 2.

<Preparation of the Emulsions>

The oil phase was heated to 70°-80° C. and allowed to melt while being agitated, to which the water phase with its ingredients having been dissolved under agitation and heating at 70°-80° C. was added to effect the emulsification. The thus obtained emulsion was cooled down to 50° C., whereupon the perfume was added, and the mixture was further allowed to cool down to a temperature of 20°-30° C.

TABLE 3

| Component | Inventive Products | | Comparative Products | |
|---|---|---|---|---|
| | E | F | G | H |
| Oil Phase | | | | |
| Octyldodecyl mirystate | 18.0 | 18.0 | 18.0 | 18.0 |
| Liquid paraffin | 10.0 | 10.0 | 10.0 | 10.0 |
| Monolauryl phosphate | 0.5 | — | — | — |
| Monocetyl phosphate | — | 1.0 | — | — |
| Cetanol | 0.5 | 0.5 | — | 1.0 |
| α-monopalmityl glyceryl ether | 2.0 | — | — | 2.0 |
| α-monostearyl glyceryl ether | — | 2.0 | 2.0 | — |
| Stearic acid | — | 0.5 | 1.0 | 1.0 |
| Water Phase | | | | |
| L-arginine | 0.2 | 0.5 | 0.5 | 0.5 |
| Methyl paraben | 0.1 | 0.1 | 0.1 | 0.1 |
| Ion exchanged water | balance | balance | balance | balance |
| Perfume | small amount | small amount | small amount | small amount |

TABLE 4

| | Inventive Products | | Comparative Products | |
|---|---|---|---|---|
| | E | F | G | H |
| State of emulsion | Good | Good | Pretty Good | Rather Bad |
| Particle size of emulsion (μm) | 1.5 | 1.3 | 3.8 | 7.6 |
| Appearance immediately after preparation | Good | Good | Pretty Good | Rather Bad |
| Stability after stored for one month: | | | | |
| at room temp. | Good | Good | Good | Rather Bad |
| at 40° C. | Good | Good | Pretty Good | Rather Bad |
| Organoleptic Evaluation * | | | | |
| Easiness in taking out from bottles | E | E | B | B |
| Spreadability of the emulsion | E | E | RB | B |
| Fitness to the skin | E | E | RB | B |

* Organoleptic Evaluation
E: Excellent
PG: Pretty Good
RB: Rather Bad
B: Bad

Figure 2:
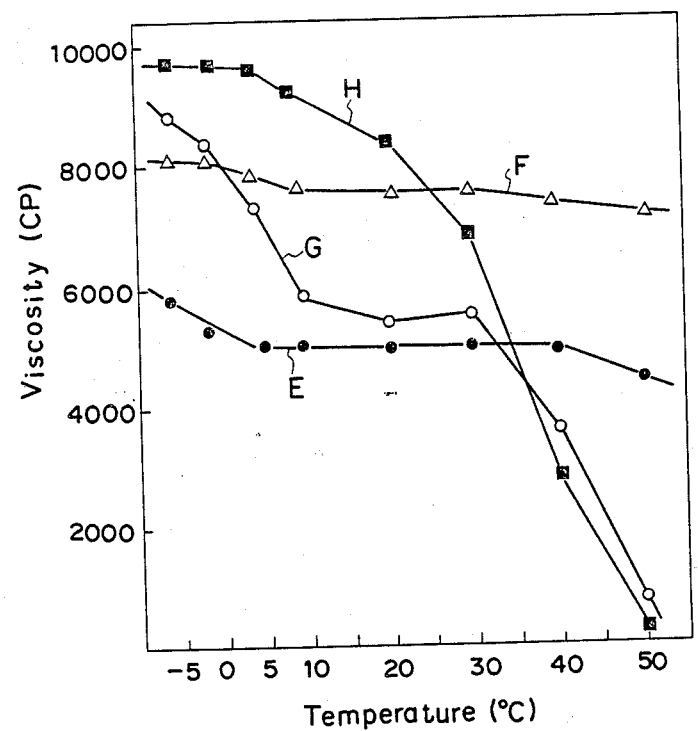

The emulsion compositions E and F containing L-arginine salt of a higher aliphatic phosphate and α-monostearyl glyceryl ether in combination, even if further added with emulsification assistant agents like fatty acids or higher alcohols, exhibited a good state of emulsion as shown in Table 4, and further as evidenced by FIG. 2, their viscosities were almost constant at the temperatures range of between −5° C. and 50° C. In contrast, the comparative compositions G and H became hard at lower temperature and their viscosities decreased conspicuously at higher temperatures.

Example 3

Night Cream

| Formulation | |
|---|---|
| (Oil Phase) | |
| Petrolatum | 10.0 (%) |
| Olive oil | 20.0 |
| α-monopalmityl glyceryl ether | 6.0 |
| Solid Paraffin | 5.0 |
| Monocetyl phosphate | 2.0 |
| Butyl paraben | 0.1 |
| (Water Phase) | |
| Methyl paraben | 0.1 |
| Dipropylene glycol | 5.0 |
| L-arginine | 1.0 |
| Water | balance |
| (Perfume, Colorants) | small amounts |

Method for the preparation

The oil phase was melted under heating at 75°-80° C. and agitated to obtain a homogeneous mixture, to which the water phase heated to dissolve its components was added while agitating at 70°-80° C. to cause the emulsification to occur. The resultant emulsion was cooled down to 50° C., added with a perfume and colorants, and further cooled down to a temperature of 20°-30° C. while agitating to obtain the night cream.

Example 4

Nourishing Emulsion

| Formulation | |
|---|---|
| (Oil Phase) | |
| Liquid paraffin | 8.0 (%) |
| Petrolatum | 6.0 |
| α-monopalmityl glyceryl ether | 1.5 |
| Stearic acid | 1.2 |
| Palmitic acid | 0.8 |
| Butyl paraben | 0.1 |
| (Water Phase) | |
| Methyl paraben | 0.1 |
| L-arginine salt of monostearyl phosphate | 1.0 |
| Carboxyvinyl polymer | 0.1 |
| 1,3-butylene glycol | 5.0 |
| potassium hydroxide | 0.003 |
| Water | balance |
| (Perfume) | small amounts |

Method for the preparation

The oil phase was melted under heating at 75°-80° C. and agitated to obtain a homogeneous mixture, to which the water phase heated to dissolve its components was added while agitating at 70°-80° C. to cause the emulsification to occur. The resultant emulsion was cooled down to 50° C., added with a perfume, and further cooled down to a temperature of 20°-30° C. while agi-

Example 5

Foundation

| Formulation | |
|---|---|
| (Oil Phase) | |
| Octyldodecyl myristate | 6.0 (%) |
| Solid paraffin | 8.0 |
| Cetanol | 4.0 |
| POE (40) hydrogenated castor oil | 1.0 |
| Monolauryl phosphate | 1.0 |
| α-monostearyl glyceryl ether | 2.0 |
| Butyl paraben | 0.1 |
| (Water Phase) | |
| Diglycerine | 6.0 |
| L-arginine | 0.65 |
| Sodium benzoate | 0.6 |
| Montmorillonite | 1.0 |
| Titanium oxide | 6.0 |
| Kaolin | 2.0 |
| Iron oxide | 3.0 |
| Talc | 8.0 |
| Water | balance |
| (Perfume) | small amounts |

Method for the preparation

The oil phase was melted under heating at 75°–80° C. and agitated to obtain a homogeneous mixture, to which the water phase, heated to 70°–75° C. and with its powder ingredients being homogeneously dispersed by a dispersing device, was added while agitating to cause the reaction and emulsification to occur. The resultant emulsion was cooled down to 50° C., added with a perfume, and further cooled down to a temperature of 20°–30° C. while agitating. The product was further treated with a homogenizer to complete thorough emulsification and obtain the foundation cream.

Example 6

Cold Cream

| Formulation | |
|---|---|
| (Oil Phase) | |
| Liquid paraffin | 45.0 (%) |
| Cerecine | 3.0 |
| Microcrystalline wax | 3.0 |
| α-monostearyl glyceryl ether | 2.0 |
| Monolauryl phosphate | 0.5 |
| POE (20) sorbitan monostearate | 1.8 |
| Sorbitan monostearate | 2.7 |
| Butyl paraben | 0.1 |
| (Water Phase) | |
| Methyl paraben | 0.1 |
| L-arginine | 0.3 |
| Dipropylene glycol | 10.0 |
| Water | balance |

| Formulation | |
|---|---|
| (Perfume) | small amounts |

Method for the preparation

The oil phase was melted under heating at 75°–80° C. and agitated to obtain a homogeneous mixture, to which the water phase heated to 70°–80° C. was added under agitation to cause the emulsification to occur. The resultant emulsion was cooled down to 50° C., added with a perfume, and further cooled down to a temperature of 20°–30° C. with continued agitation to obtain the the cold cream.

Having now fully described the invention, it will be apparent to one of the ordinary skill in the art that many changes and modifications can be made thereto without departing from the spirit or scope of the invention as set forth herein.

What is claimed is:

1. An oil in water type emulsion composition comprising:
   (A) 0.01 to 5 wt.% of a basic amino acid salt of a higher aliphatic phosphate represented by the following formula (I)

$$R_1-O-\underset{\underset{OH}{|}}{\overset{\overset{O}{\|}}{P}}-OH \quad (I)$$

in which $R_1$ is an alkyl or alkenyl group having from 12 to 22 carbon atoms, said basic amino acid being selected from the group consisting of arginine, lysine, ornithine, histidine, and δ-hydroxylysine, and (B) an α-monoalkyl glyceryl ether, in an amount of 0.1 to 20 times by weight of said component (A), which is represented by the following formula (II):

$$\begin{array}{l} R_2-O-CH_2 \\ \phantom{R_2-O-}|\\ \phantom{R_2-O-}CH-OH \\ \phantom{R_2-O-}| \\ \phantom{R_2-O-}CH_2OH \end{array} \quad (II)$$

in which $R_2$ is an alkyl group having from 12 to 24 carbon atoms.

2. An oil in water type emulsion composition as claimed in claim 1 wherein the content of oil is from 1 to 70 wt.%, and the content of water is from 20 to 90 wt.%.

3. An oil in water type emulsion composition as claimed in claims 1 or 2, in which said basic amino acid is L-arginine.

4. An oil in water type emulsion composition as claimed in claims 1 or 2, in which said α-monoalkyl glyceryl ether is α-monopalmityl glyceryl ether or α-monostearyl glyceryl ether.

* * * * *